(12) United States Patent
Heberer (10) Patent No.: US 8,821,485 B2
(45) Date of Patent: Sep. 2, 2014

(54) EMPLOYING A SECONDARY SHEATH WITH AN ABLATION CATHETER

(75) Inventor: Joann Heberer, Portola Valley, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 915 days.

(21) Appl. No.: 12/695,268

(22) Filed: Jan. 28, 2010

(65) Prior Publication Data

US 2010/0191231 A1 Jul. 29, 2010

Related U.S. Application Data

(60) Provisional application No. 61/148,258, filed on Jan. 29, 2009.

(51) Int. Cl.
| | |
|---|---|
| A61B 18/02 | (2006.01) |
| A61B 18/12 | (2006.01) |
| A61M 25/00 | (2006.01) |
| A61M 25/06 | (2006.01) |
| A61B 18/14 | (2006.01) |
| A61B 19/00 | (2006.01) |
| A61M 25/01 | (2006.01) |
| A61B 18/00 | (2006.01) |

(52) U.S. Cl.
CPC .............. *A61M 25/00* (2013.01); *A61B 19/201* (2013.01); *A61B 18/02* (2013.01); *A61M 25/0138* (2013.01); *A61M 25/0662* (2013.01); *A61M 25/0152* (2013.01); *A61M 2025/0681* (2013.01); *A61B 2018/0022* (2013.01); *A61B 18/1492* (2013.01); *A61B 2018/0262* (2013.01); *A61B 2018/0212* (2013.01)
USPC .............................................. 606/21; 606/41

(58) Field of Classification Search
USPC ......................................... 606/20–26, 34, 41
See application file for complete search history.

(56) References Cited

U.S. PATENT DOCUMENTS

| | | | | |
|---|---|---|---|---|
| 4,311,143 | A | * | 1/1982 | Komiya ........................... 606/47 |
| 5,545,193 | A | * | 8/1996 | Fleischman et al. ............ 607/99 |
| 5,807,395 | A | * | 9/1998 | Mulier et al. .................... 606/41 |
| 5,881,727 | A | | 3/1999 | Edwards |
| 5,906,612 | A | * | 5/1999 | Chinn ............................. 606/20 |
| 6,200,315 | B1 | * | 3/2001 | Gaiser et al. .................... 606/41 |
| 6,256,540 | B1 | * | 7/2001 | Panescu et al. ................ 607/122 |
| 6,327,505 | B1 | * | 12/2001 | Medhkour et al. .............. 607/99 |

(Continued)

FOREIGN PATENT DOCUMENTS

| | | |
|---|---|---|
| EP | 0711573 A1 | 5/1996 |
| WO | 2005112801 A2 | 12/2005 |

*Primary Examiner* — Michael Peffley
*Assistant Examiner* — Daniel Fowler
(74) *Attorney, Agent, or Firm* — Seager, Tufte & Wickhem, LLC (57) ABSTRACT

A method of performing a catheter-based procedure can include introducing a delivery sheath inside a patient's body and advancing a secondary sheath through the delivery sheath, toward a treatment site inside the patient's body. The secondary sheath can be distinct from the delivery sheath, coaxial to the delivery sheath along at least a portion of a length of the delivery sheath, and can have a default linear shape that is substantially free of radial bias. The method can further include introducing a catheter through the delivery sheath and secondary sheath, to the treatment site, and performing a procedure at the treatment site with the catheter. Performing the procedure can include performing the procedure while maintaining at a relatively fixed position the secondary sheath.

24 Claims, 4 Drawing Sheets

(56) References Cited

U.S. PATENT DOCUMENTS

| | | |
|---|---|---|
| 6,432,102 B2 * | 8/2002 | Joye et al. .................. 606/21 |
| 6,602,276 B2 * | 8/2003 | Dobak et al. ................ 607/105 |
| 7,682,319 B2 | 3/2010 | Martin et al. |
| 2001/0044624 A1 * | 11/2001 | Seraj et al. ................... 606/41 |
| 2008/0004488 A1 * | 1/2008 | Hjelle et al. .................. 600/37 |
| 2008/0051703 A1 | 2/2008 | Thornton et al. |
| 2008/0119785 A1 | 5/2008 | Ramsey et al. |
| 2009/0105742 A1 | 4/2009 | Kurth et al. |
| 2009/0156995 A1 | 6/2009 | Martin et al. |

* cited by examiner

EMPLOYING A SECONDARY SHEATH WITH AN ABLATION CATHETER

CROSS-REFERENCE TO RELATED APPLICATION

This application claims priority under 35 U.S.C. §119(e) to U.S. Provisional Patent Application Ser. No. 61/148,258, filed on Jan. 29, 2009, the entire contents of which are hereby incorporated by reference.

BACKGROUND

A number of serious medical conditions may be treated in a minimally invasive manner with various kinds of catheters designed to reach treatment sites internal to a patient's body. One such medical condition is atrial fibrillation—a serious medical condition that results from abnormal electrical activity within the heart. This abnormal electrical activity may originate from various focal centers of the heart and generally decreases the efficiency with which the heart pumps blood. It is believed that some of these focal centers reside in the pulmonary veins of the left atrium. It is further believed that atrial fibrillation can be reduced or controlled by structurally altering or ablating the tissue at or near the focal centers of the abnormal electrical activity.

One method of ablating tissue of the heart and pulmonary veins to control atrial fibrillation includes delivering radio-frequency (RF) energy to the tissue to be ablated. In particular, high frequency energy can be employed, for example, to cause ionic agitation and frictional heat in targeted tissue, causing permanent damage to the tissue. Once damaged, the tissue may no longer propagate or source electrical signals, and the fibrillation may be treated or reduced. The RF energy can be delivered by an RF catheter having an RF source at a distal treatment end that is positioned at a treatment site inside a patient during a treatment procedure.

Another method of ablating tissue of the heart and pulmonary veins to control atrial fibrillation includes delivering cryotherapy to the tissue to be ablated. Cryotherapy may also cause permanent alteration to treated tissue, preventing the treated tissue from propagating or sourcing electrical signals, thereby reducing or eliminating atrial fibrillation. Cryotherapy may be delivered to appropriate treatment sites inside a patient's heart and circulatory system by a cryotherapy catheter. A cryotherapy catheter generally includes a treatment member at its distal end, such as an expandable balloon or metal tip having a cooling chamber inside. A cryotherapy agent may be provided by a source external to the patient at the proximal end of the cryotherapy catheter and delivered distally, through a lumen in an elongate member, to the cooling chamber where it is released. Release of the cryotherapy agent into the chamber cools the chamber, the balloon's outer surface, and tissue that is in contact with the outer surface, to perform ablation. The cryotherapy agent may be exhausted proximally through an exhaust lumen in the elongate member to a reservoir external to the patient.

SUMMARY

In some catheter-based procedures that employ a delivery sheath, use of a secondary sheath inside the delivery sheath can facilitate treatment at multiple treatment sites without a mid-procedure exchange of the delivery sheath. The secondary sheath may help stabilize and maintain position of both the delivery sheath and the catheter during the procedure, and may further simplify routing of the catheter to the multiple treatment sites.

A method of performing a catheter-based procedure can include introducing a delivery sheath inside a patient's body and advancing a secondary sheath through the delivery sheath, toward a treatment site inside the patient's body. The secondary sheath can be distinct from the delivery sheath, coaxial to the delivery sheath along at least a portion of a length of the delivery sheath, and can have a default linear shape that is substantially free of radial bias. The method can further include introducing a catheter through the delivery sheath and secondary sheath, to the treatment site, and performing a procedure at the treatment site with the catheter. Performing the procedure can include performing the procedure while maintaining at a relatively fixed position the secondary sheath.

In some implementations, the delivery sheath is steerable and also has a default linear shape that is substantially free of radial bias. The method can further include employing the secondary sheath to position the catheter at the treatment site. The method can further include employing the secondary sheath to maintain position of the catheter at the treatment site during the procedure. The method can further include advancing a tip of the secondary sheath beyond a distal end of the delivery sheath, and employing the tip to cross a tissue membrane. The method can further include advancing a guidewire towards the treatment site, wherein introducing the delivery sheath comprises introducing the delivery sheath over the guidewire.

In some implementations, the catheter is a balloon catheter. The method can further include deflating a balloon portion of the balloon catheter following the procedure, and employing the secondary sheath to groom the balloon portion for withdrawal into the delivery sheath after the balloon portion is deflated. Employing the secondary sheath to groom the balloon portion can include advancing the secondary sheath over at least a portion of the balloon portion to collapse material of the balloon portion toward an axis of the balloon portion.

A system for performing a catheter-based procedure can include a delivery sheath; a secondary sheath that is distinct from the delivery sheath, that has a portion configured to be coaxially advanced through the delivery sheath during a procedure, and that has a default linear shape that is substantially free of radial bias; and a catheter configured to, during the procedure, be advanced through the secondary sheath and delivery sheath and deliver therapy to a treatment site inside a patient's body while the secondary sheath is maintained at a relatively fixed position.

In some implementations, the system can further include a guidewire. At least one of the delivery sheath, secondary sheath or catheter can be configured to be advanced toward the treatment site over the guidewire. In some implementations, the catheter is a balloon catheter. The catheter can be configured to delivery cryotherapy to the treatment site. The catheter can be configured to deliver radio-frequency energy to the treatment site.

The secondary sheath can include a distal tip having a tapered outer diameter. The distal tip can include a radio-opaque material. The secondary sheath can include a flexible distal segment and a proximal force-transmitting segment. The flexible distal segment can have a greater flexibility than the proximal force-transmitting segment. The flexible distal segment can include a hypotube. The proximal force-transmitting segment can include a braided construction. The delivery sheath can be steerable. The delivery sheath can have a lubricious inner surface. The inner surface can include silicone-impregnated HDPE (high-density polyethylene). In some implementations, the secondary sheath has a length that is shorter than the length of the delivery sheath, and the secondary sheath further includes a push member. A combined length of the secondary sheath and the push member can exceed a length of the delivery sheath.

The details of one or more implementations are set forth in the accompanying drawings and the description below. Other features, objects, and advantages will be apparent from the description and drawings, and from the claims.

BRIEF DESCRIPTION OF DRAWINGS

Like reference symbols in the various drawings indicate like elements.

DETAILED DESCRIPTION

In some catheter-based procedures that employ a delivery sheath, use of a secondary sheath inside the delivery sheath can facilitate treatment at multiple treatment sites without a mid-procedure exchange of the delivery sheath. The secondary sheath may help stabilize and maintain position of both the delivery sheath and the catheter during the procedure, and may further simplify routing of the catheter to the multiple treatment sites.

Medical devices, such as catheters, can be employed to treat various sites internal to a patient's body. For example, an ablation catheter can be used to ablate tissue in a patient's left atrium (e.g., pulmonary vein tissue) to treat atrial fibrillation. In some procedures, a delivery sheath is used to guide the medical device to the region of treatment. The delivery sheath can have the form of a hollow tube or channel that can be initially disposed in the patient. Subsequently, a medical device (e.g., an ablation catheter) can be guided through the delivery sheath to the treatment site. Use of a delivery sheath can facilitate subsequent use of multiple different medical devices (e.g., multiple catheters having different sizes or functions), which can be exchanged, one for another, during a procedure.

Figures 1A, 1B, 1C:
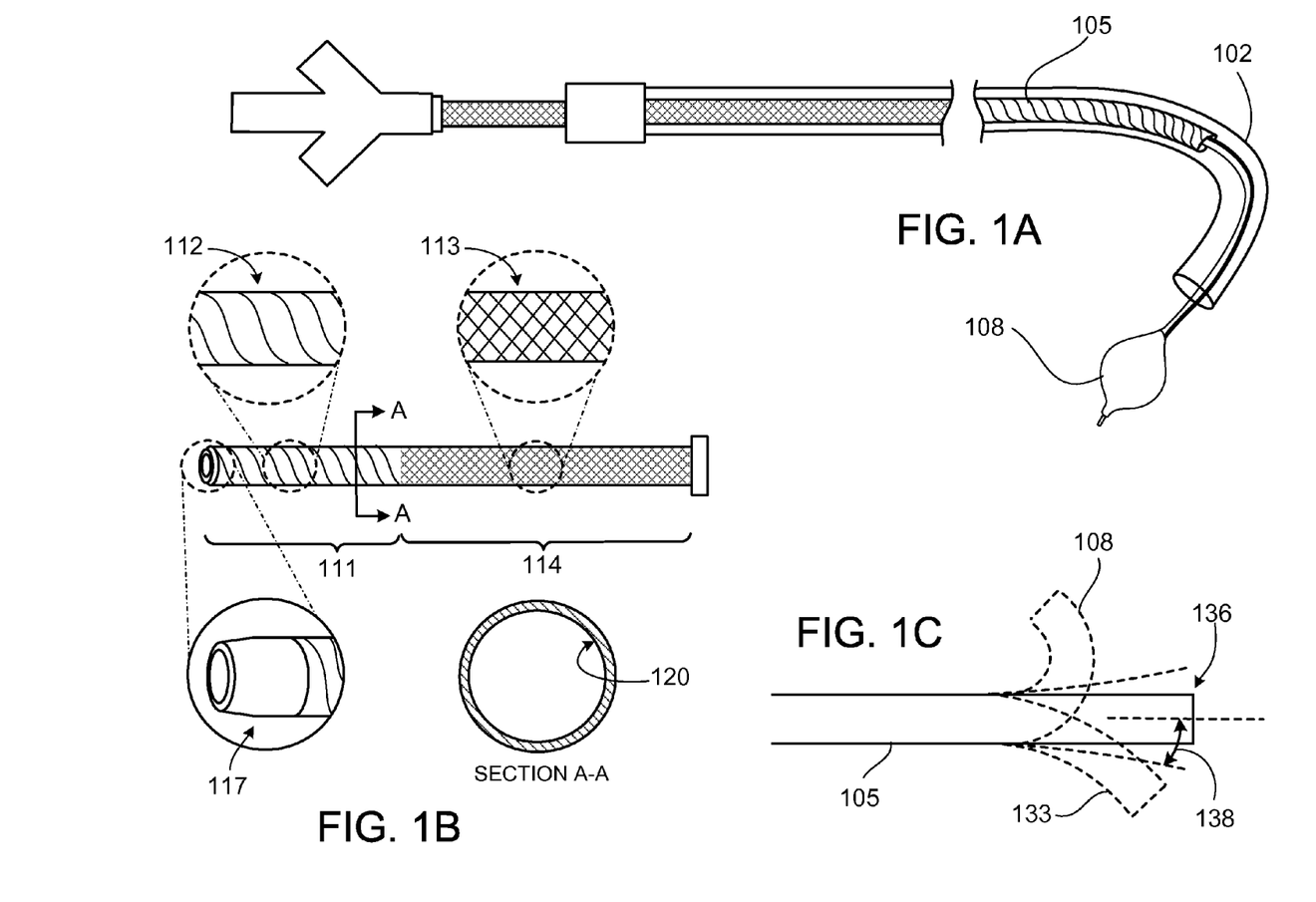
FIG. 1A illustrates an example secondary sheath that can be used in delivering therapy to a treatment site internal to a patient.
FIGS. 1B and 1C illustrate additional details of the secondary sheath shown in FIG. 1A.

FIG. 1A illustrates an example secondary sheath 105 that can be used in a procedure for treating internal tissue of a patient. For context, the secondary sheath 105 is shown with a delivery sheath 102 and a medical device—in this example, a balloon catheter 108. As described below with reference to FIG. 3, the delivery sheath 102 may be routed to or near a treatment site internal to a patient (e.g. the patient's left atrium). More precisely, a distal end of the delivery sheath 102 can be routed, generally with distal ends of a corresponding secondary sheath 105 and catheter 108, to a site internal to a patient. A proximal end of the secondary sheath 105 remains outside the patient, along with proximal ends of the corresponding delivery sheath 102 and catheter 108. In some implementations, the delivery sheath 102 is steerable. Generally, as depicted in FIG. 1A, the secondary sheath 105 is distinct from the delivery sheath 102 and is coaxial to the delivery sheath 102 along at a least a portion of the length of the delivery sheath 102.

FIG. 1B illustrates additional details of the secondary sheath 105 shown in FIG. 1A. As depicted by variation in shading, the secondary sheath 105 can vary in stiffness over its length. For example, the secondary sheath 105 can have a relatively flexible distal portion 111 and a stiffer proximal portion 114. In some implementations, the flexible distal portion 111 is well suited for navigating turns in a medical device's path to a treatment region (see FIG. 3 and the corresponding description below); the stiffer proximal portion 114 may be somewhat flexible as well, but also well-suited for transmitting torque and axial force along its length.

In some implementations, the flexible distal portion 111 has a metallic ribbon coil construction (not shown) or hypotube construction 112. The stiffer proximal portion 114 can have a braided-shaft construction 113, or another appropriate construction that provides some flexibility, as well as efficient transmission of torque and axial force.

The relative lengths of the stiffer proximal portion 114 and more flexible distal portion 111 can vary. In some implementations, it can be advantageous to have a long stiffer portion 114 and a relatively shorter flexible portion 111; in other implementations, it can be advantageous to have a longer flexible portion 111. Although two regions of varying stiffness are shown, the secondary sheath 105 can include more regions of varying stiffness. For example, the secondary sheath 105 can include three, four, five, or more regions of increasing flexibility. As another example, the secondary sheath 105 may have a stiffness gradient that varies substantially continuously from one point on the secondary sheath 105 to another, more distal point on the secondary sheath 105.

In some procedures, it can be advantageous to advance the secondary sheath 105 ahead of the delivery sheath 102, at least at some instances in the procedure. In such instances, a tapered distal tip 117 of the secondary sheath 105 can be particularly advantageous. For example, the tapered distal tip 117 can be advanced inside a patient and across a tissue membrane that must be penetrated to reach an intended treatment site. More specifically, in procedures that target a patient's left atrium, the tapered distal tip 117 can be used to cross the septal wall, possibly after a transseptal needle is employed to create an access point. After the tapered distal tip 117 crosses the membrane, the larger delivery sheath 102 may be more easily advanced through the membrane. Subsequently, if the delivery sheath 102 becomes dislodged (e.g., passes back through the septal wall during a procedure in the left atrium), the secondary sheath 105 can again be advanced through the tissue membrane, and the delivery sheath 102 can be advanced over the secondary sheath 105.

In some implementations, an inner surface 120 of the secondary sheath 105 is highly lubricious, such that a medical device (e.g., an ablation catheter) can be easily advanced through the secondary sheath 105. For example, in some implementations, the inner surface 120 of the secondary sheath is a high density polyethylene (HDPE), impregnated with silicon or other lubricious material.

In some procedures, the delivery sheath itself is replaced mid-procedure with another delivery sheath. In particular, for example, one delivery sheath having a first pre-biased curvature at its distal end can be employed during one phase of a procedure to reach a first treatment region; subsequently, the delivery sheath can be exchanged for a second delivery sheath having a second pre-biased curvature at its distal end, which may facilitate treatment of a second treatment region. The distal end of a delivery sheath having a pre-biased curvature can be flexible, such that the delivery sheath can be routed through straight or curved vessels. Once in an open cavity (e.g., a patient's atrium, aorta, or other thoracic cavity), the distal end can spring to its pre-biased shape to facilitate navigation to or through particular regions of the cavity.

FIG. 1C illustrates two examples of pre-biased curvatures for the distal end of the delivery sheath 105. In particular, the configuration 130 illustrates a pre-biased curvature of approximately 135°, which may be well-suited for reaching a pulmonary vein that is close to in-line (e.g., in the same plane as) with an access point in the septal wall. The configuration 133 illustrates a different pre-biased curvature of approximately 30°, which may be well-suited for reaching a pulmonary vein that is opposite and slightly above or below an access point in the septal wall. Configuration 136 illustrates a default linear shape that is substantially free of radial bias. For example, the configuration 136 depicts a configuration for the delivery sheath 105 that is straight by default, or straight within a small threshold 138 (e.g., within typical manufacturing margins, or within one or two degrees, of not having any radial bias), unlike the configurations 130 and 133.

In some procedures (e.g., procedures performed inside a patient's beating heart), the distal end of the delivery sheath may be prone to becoming dislodged—for example, as the medical device is routed through the introducer sheath, or at some other point during the procedure. The secondary sheath may stabilize and help maintain position of both the delivery sheath and the medical device during the procedure. In addition, different medical devices may be more easily routed through than delivery sheath than other devices. Specifically, for example, in some procedures, a larger-diameter catheter may be more easily routed through a delivery sheath than a small-diameter catheter; in other procedures the opposite may be true.

Figure 2:
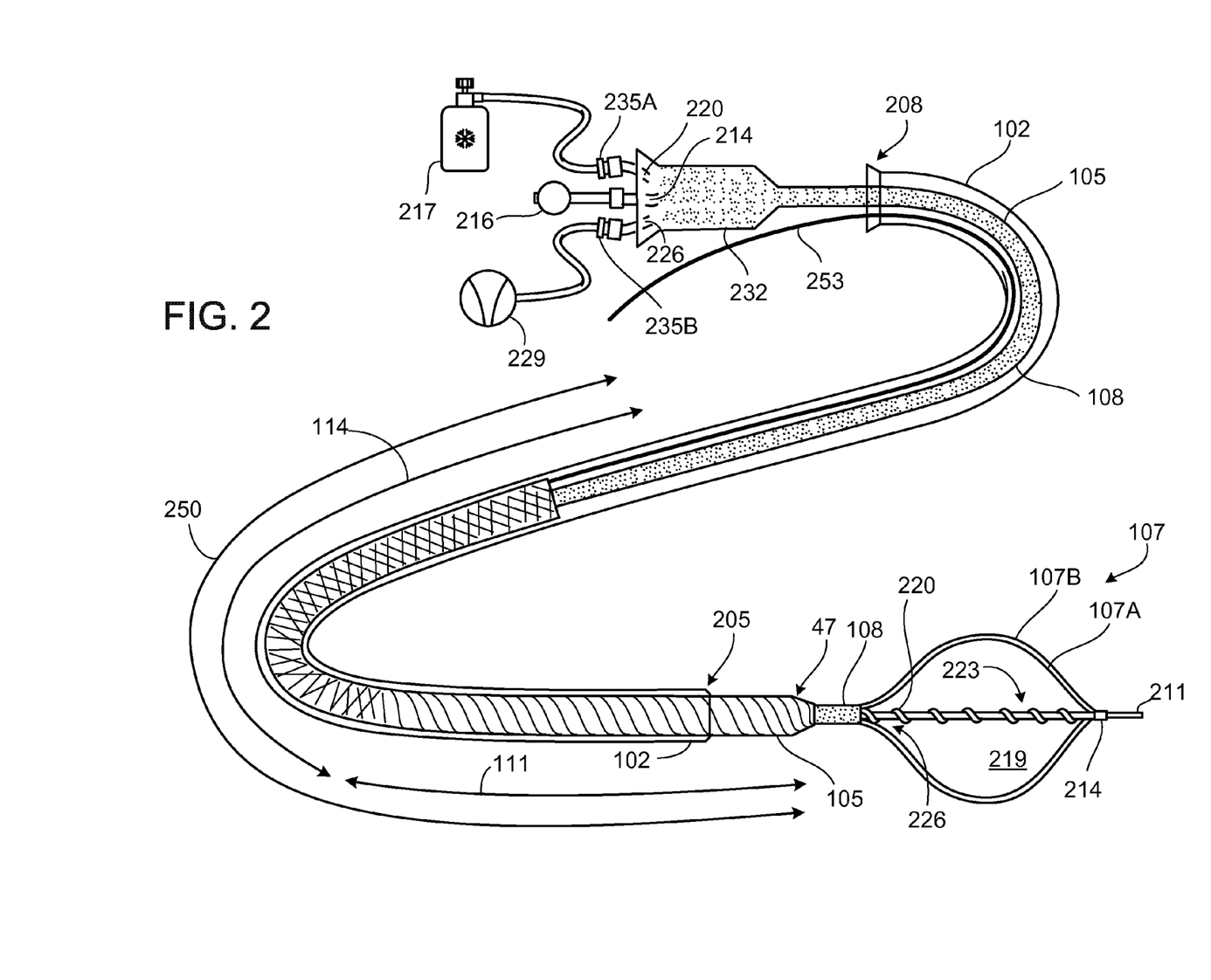
FIG. 2 illustrates the secondary sheath of FIG. 1A as it might be used with a delivery sheath and balloon catheter.

FIG. 2 illustrates additional details of the example secondary sheath 105, as it may be used with the delivery sheath 102 and balloon catheter 108. For purposes of illustration, various details of a specific type of balloon catheter (e.g., a cryotherapy balloon catheter 108) are illustrated and described. The reader will appreciate, however, that procedures employing various other kinds of catheters, or other medical devices, can benefit from the secondary sheath 105.

As shown in FIG. 2, the secondary sheath 105 may only be coaxial along a portion of the length of the delivery sheath 102. That is, the secondary sheath 105 can include a coaxial portion 250 and a push wire 253 that provides a technician with flexibility in positioning the coaxial portion 250 where it is most helpful. In some procedures, it may be advantageous to "park" the stiffer proximal region 114 in a relatively straight region of a vessel through which the secondary sheath 105 is routed, possibly extending just through a curve or bend in the vessel, as depicted. In other procedures, it may be advantageous to dispose the secondary sheath 105 more proximally or more distally.

The delivery sheath 102 shown in FIG. 2 may be steerable (steering components not shown), and it may have specific characteristics. For example, delivery sheaths may be available in varying diameters, such as 8.5 Fr (French), 10 Fr, 11 Fr, etc.; varying lengths, such as 60 cm, 65 cm, 71 cm, 78 cm, 90 cm, etc.; and having distal ends that are biased in various shapes, such as, for example, in a 15° curve, a 55° curve, a short 120° curve, a long 120° curve, etc. Different delivery sheaths may be configured for different procedures. For example, a delivery sheath having one biased curvature may be particularly effective for guiding a cryo balloon to a patient's pulmonary veins to treat atrial fibrillation, while a delivery sheath having a different biased curvature may be particularly effective for guiding a stent-delivery balloon. In some procedures, a delivery sheath that is steerable but unbiased at its distal end is employed, and such a delivery sheath may be employable in a wide range of procedures.

In some implementations, as depicted in FIG. 2, a distal tip 205 of the delivery sheath 102 is also slightly tapered, to facilitate navigation of the tip 205 through a patient's vasculature, or to facilitate crossing of tissue membranes of the patient (e.g., the septal wall, during a procedure to treat atrial fibrillation). The proximal end 208 may also be tapered to more easily receive other medical devices, such as the balloon catheter 108 that is shown disposed in the delivery sheath 102.

A balloon catheter 108 is shown inside the delivery sheath 102. In the example of FIG. 2, the balloon catheter 108 is an over-the-wire cryotherapy balloon catheter, having a guidewire 211 disposed inside a guidewire lumen 214. The reader will appreciate that other types of catheters, and other types of medical devices, can be employed with the secondary sheath 105. For example, in other implementations, the balloon catheter 108 may not employ a guidewire 211. As another example, in other implementations, the balloon catheter 108 could be a radio-frequency (RF) ablation catheter that remodels tissue with RF energy rather than by extracting heat using a cryogenic agent.

In the example implementation shown in FIG. 2, cryogenic fluid can be delivered from an external source 217 to a balloon 107 (or other distally disposed treatment component) through a supply lumen 220, and released inside the interior chamber 219, through a cooling device 223 (e.g., a coiled portion of the supply lumen 220 having various orifices through which certain cryogenic agents can exit and undergo a liquid-to-gas phase change that cools the balloon 107 by the Joule-Thomson effect). Gas resulting from the cryogenic fluid being released and changing phase inside the chamber 219 can be exhausted through a separate exhaust lumen 226. In particular, for example, in some implementations, gas is exhausted through an exhaust lumen 226 to an external vacuum pump 229.

To facilitate coupling the catheter 108 to external equipment, such as the source 217 of a cryogenic agent or the vacuum pump 229, the catheter 108 can include a port component 232 having a number of coupling members 235A and 235B. The coupling members 235A and 235B can, in some implementations, terminate lumens that are internal to the catheter shaft (e.g., a supply lumen 220 and an exhaust lumen 226) with connectors (e.g., industry-standard medical connectors, proprietary medical connectors, other connectors, etc.) that facilitate connection of the lumens 220 and 226 to the external equipment (e.g., with medical tubing). As depicted in one example, the port component 232 can also provide access to the guidewire lumen 214 and corresponding guidewire 211. As shown in FIG. 2, the port component 232 is merely exemplary. Other connections and configurations are possible and contemplated (e.g., connections for pressure sensor(s), electrical sensor(s), multiple vacuum ports, etc.).

As depicted, the treatment balloon 107 can include two separate balloons 107A and 107B disposed on the end of a catheter shaft 210. The balloons 107A and 107B can inflate and deflate together. In some implementations, the second balloon 107B functions as a safety balloon 107B. That is, in the event that the balloon 107A ruptures or otherwise fails, the safety balloon 107B can prevent agents inside the interior chamber 219 (e.g., cryogenic agents) from directly contacting body tissue internal to the patient and can similarly prevent body tissue and body fluids from reaching the interior chamber 219. In some implementations, a separate vacuum lumen (not shown) is provided between the balloons 107A and 107B, and can be used to apply a constant vacuum force between the balloons 107A and 107B. In the event that the inner balloon 107A ruptures, the constant vacuum force can continue to evacuate any liquid and/or gas inside the interior chamber 219 and prevent the same from coming into direct contact with tissue internal to the patient. If either inner balloon 107A or outer balloon 107B ruptures, a sensor that monitors the vacuum force between the balloons 107A and 107B can detect a change in pressure and can cause an alarm to be generated or corrective action to be taken.

Figure 3:
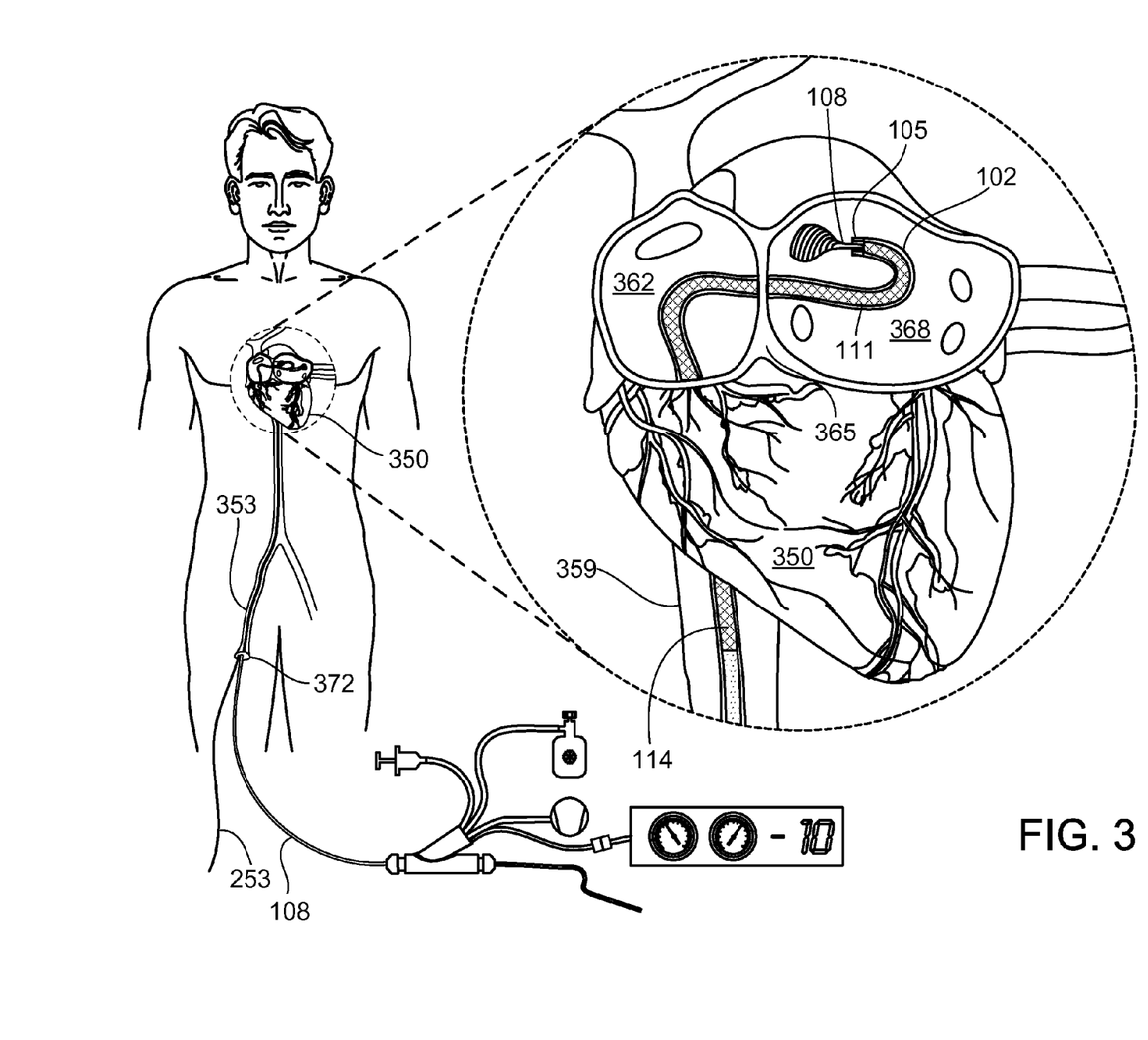
FIG. 3 illustrates an example application in which the secondary sheath of FIG. 1A may be employed.

FIG. 3 illustrates an example application in which the secondary sheath 105 illustrated and described above may be employed. Additional details of the secondary sheath 105 are described with reference to the example application. In this example, the catheter 108 can be employed to deliver cryotherapy to the left atrium 368 of a patient's heart 350 in order to treat atrial fibrillation.

To locate the catheter 108 in the patient's left atrium 368, a medical practitioner may obtain access to the patient's circulatory system at the patient's femoral vein 353. In particular, the medical practitioner may insert a sleeve or introducer sheath 372 into the patient's femoral vein 353 to keep an access point open during the procedure. The medical practitioner may then advance the delivery sheath 102 through the introducer sheath 372, into the femoral vein 353, through the inferior vena cava 359, and into the patient's right atrium 362. The medical practitioner may then puncture the septum 365. In particular, the medical practitioner may route a transseptal needle (not shown) to the right atrium 362, puncture the septum 365 with the transseptal needle to create an access point, withdraw the transseptal needle, and advance the secondary sheath 105 through the access point, using the distal tip 117 to penetrate and expand the access point. The delivery sheath 102 can be routed over the secondary sheath 105 and through the access point, and the catheter 108 can be routed through the delivery sheath 102 and the secondary sheath 105. Once the catheter 108 is located in the left atrium 368, it can be precisely positioned at the treatment site (e.g., an ostium or antrum of one of the pulmonary veins), and ablation energy (e.g., RF energy or cryotherapy) can be delivered.

The secondary sheath 105 can be used to help stabilize the catheter 108 during a procedure such as the one just described. In particular, the stiffer proximal portion 114 of the secondary sheath 105 can stabilize the delivery sheath 102 and catheter 108 during a procedure. More specifically, given that procedures are often performed within a beating heart, or in vessels that are actively conveying blood, the additional rigidity provided by the secondary sheath 105 can help stabilize the delivery sheath 102 and catheter 108 against structures (e.g., the septal wall) or in vessels. In some procedures, the secondary sheath 105 is anchored against a structure or in a vessel, and the secondary sheath 105 is maintained at a relatively fixed position during the procedure. That is, the secondary sheath 105 may move with other structures that are moving, such as a beating heart or pulsing vessel, but relative to specific points on the heart or vessel, the secondary sheath 105 may be maintained at a substantially fixed position. The procedure may benefit from the secondary sheath 105 being employed to provide additional rigidity during the procedure, in contrast to a sheath that is configured to be removed or moved at some point during the procedure.

Even a flexible distal portion 111 can help stabilize the distal tip of a steerable delivery sheath 105. In some implementations, the added stabilization provided by the secondary sheath 105 can obviate the need for separate delivery sheaths having different pre-biased distal curvatures. Thus, with a single secondary sheath 105, it may be possible to, in the example of treating atrial fibrillation, treat both left and right superior pulmonary veins without a mid-procedure delivery sheath 102 exchange—even though, in this example, the angle of approach between the left and right superior pulmonary veins is generally very different.

In general, the secondary sheath 105 can be particularly useful in procedures in which treatment is delivered to an open cavity and requires precise placement of the treatment device without the support of surrounding body structures (e.g., the walls of a vessel being treated). The secondary sheath 105 may also be particularly useful in procedures that traditionally employ different delivery sheaths having pre-biased distal curvatures.

Figure 4:
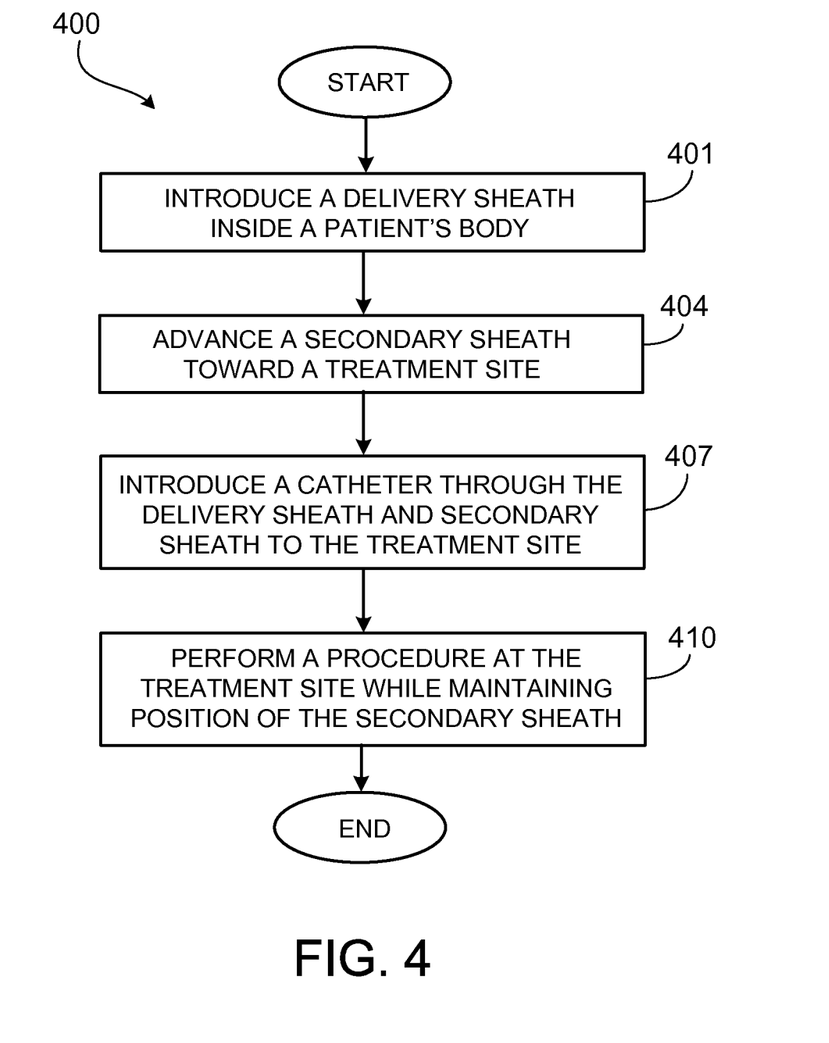
FIG. 4 is a flow diagram of an example method for delivering therapy in a catheter-based procedure, using a secondary sheath.

FIG. 4 is a flow diagram of an example method 400 for delivering therapy in a catheter-based procedure, using a secondary sheath. The method 400 can include introducing (401) a delivery sheath inside a patient's body. For example, with reference to FIG. 3, the delivery sheath 105 can be inserted into a patient's femoral vein 353 and routed towards the patient's heart 350. A secondary sheath 105 can also be advanced (404) towards a treatment site inside the patient's body. For example, the secondary sheath 105 can also be advanced (404) through the patient's femoral vein 353, toward the heart 350.

The order in which the delivery sheath 102 and the secondary sheath 105 are introduced into the patient can vary by procedure. In some procedures, the delivery sheath 102 is initially introduced, and the secondary sheath 105 is subsequently advanced. Such a method may be employed particularly when the secondary sheath 105 is shorter in length than the delivery sheath 102. In other procedures, both the delivery sheath 102 and the secondary sheath 105 are advanced through a patient's vasculature together. In still other procedures, the secondary sheath 105, with its smaller size and optionally tapered distal end 117, is initially advanced through at least part of the patient's vasculature, and the delivery sheath 102 is subsequently advanced over the secondary sheath 105.

After being introduced, one or both of the delivery sheath 102 and the secondary sheath 105 can be routed to the treatment site. In particular, for example, in a procedure to treat atrial fibrillation, one or both of the sheaths 102 and 105 can be advanced to the patient's right atrium 362, advanced through an access point in the patient's septal wall 365, and routed into the patient's left atrium 368. At that point, the secondary sheath 105 can be positioned in such a manner that the position of the delivery sheath 102 is stabilized. For example, a stiffer proximal portion 114 of the secondary sheath 105 may be routed through the inferior vena cava 359, right atrium 362, and septal wall 365 (e.g., to keep the distal end of the delivery sheath 105 from retracting back through the septal wall 365 as the patient's heart beats). The more flexible distal portion 111 of the secondary sheath 105 can stabilize the distal tip. More particularly, the added rigidity provided by the distal portion 111 may, in conjunction with a steering mechanism in the delivery sheath 105 and/or with a guidewire, help position the distal end of the delivery sheath 105 next to a pulmonary vein to be treated.

The method 400 can include introducing (407) a catheter through the delivery sheath and secondary sheath to the treatment site. For example, once the delivery sheath 102 and secondary sheath 105 are positioned as described above (e.g., in front of a pulmonary vein to be treated), the catheter 108 can be routed to the treatment site (e.g., the right superior pulmonary vein, as depicted in FIG. 3). At the treatment site, the catheter 108 can be employed to perform (410) a procedure. For example, with a cryotherapy catheter 108 as depicted in FIG. 2, cryotherapy can be delivered to tissue of one or more pulmonary veins in order to ablate the tissue, so as to disrupt aberrant electrical pathways that may be causing atrial fibrillation.

In some procedures, after treatment is performed (410) at one site, the delivery sheath 102, secondary sheath 105, and catheter 108 can be moved to a second treatment site (e.g., another pulmonary vein ostium/antrum), and the treatment can be performed (410) at that site. In some procedures, the secondary sheath 105 obviates the need to employ a different delivery sheath 102 to provide treatment at the second site. For example, rather than requiring two separate delivery sheaths, having pre-biased distal curvatures of, for example, 150° and 55° to reach, respectively, a patient's right superior pulmonary vein and left inferior pulmonary vein, a single delivery sheath 102, in conjunction with the secondary sheath 105, may be employed to reach all four pulmonary veins.

In procedures such as the one described above, the secondary sheath 105 can serve to stabilize a substantially linear, radially-unbiased delivery sheath 102 in whatever position may be required to reach the desired treatment site. The secondary sheath 105 may also help groom the balloon portion of a balloon catheter for withdrawal into the delivery sheath 102 following a treatment procedure or cycle. For example, the secondary sheath 105 may have a rounded inner edge (not shown) that helps collapse a balloon portion as the catheter 108 is withdrawn into the delivery sheath 102 (or as the secondary sheath 105 is advanced over the balloon portion (e.g., for purposes of deflating the balloon portion)). The secondary sheath 105 may also prevent, or help prevent, the delivery sheath 102 or the catheter 108 from kinking as the catheter 108 is navigated through tortuous turns in a patient's vasculature. Advantageously, by employing a single delivery sheath 102 and secondary sheath 105, patient trauma and risk may be reduced, a procedure time may be decreased, less inventory may be maintained at a treatment center, etc.

The method illustrated in and described with reference to FIG. 4 is merely exemplary. Actions of the example method can be reordered, removed, and other actions can be added. Moreover, atrial fibrillation and ablation of the pulmonary veins to treat such a condition have been described by way of example. The reader will appreciate that a secondary sheath may be advantageously employed during many other kinds of procedures, at many other treatment sites outside of the heart.

A number of implementations have been described. Nevertheless, it will be understood that various modifications may be made without departing from the spirit and scope of this document. Accordingly, other implementations are within the scope of the following claims.

What is claimed is:

1. A method of performing a catheter-based procedure, the method comprising:
    introducing a delivery sheath inside a patient's body;
    advancing a secondary sheath through the delivery sheath, toward a treatment site inside the patient's body, wherein the secondary sheath is distinct from the delivery sheath, coaxial to the delivery sheath along at least a portion of a length of the delivery sheath, and has a default linear shape that is substantially free of radial bias, the secondary sheath having a length that is shorter than a length of the delivery sheath, the secondary sheath further comprising a push member having a distal end attached to a proximal end of the secondary sheath, wherein a combined length of the secondary sheath and the push member exceeds a length of the delivery sheath;
    introducing a catheter through the delivery sheath and secondary sheath, to the treatment site; and
    performing a procedure at the treatment site with the catheter, wherein performing the procedure comprises performing the procedure while maintaining at a relatively fixed position the secondary sheath.

2. The method of claim 1, wherein the delivery sheath is steerable and also has a default linear shape that is substantially free of radial bias.

3. The method of claim 1, further comprising employing the secondary sheath to position the catheter at the treatment site.

4. The method of claim 1, further comprising employing the secondary sheath to maintain position of the catheter at the treatment site during the procedure.

5. The method of claim 1, further comprising advancing a tip of the secondary sheath beyond a distal end of the delivery sheath, and employing the tip to cross a tissue membrane.

6. The method of claim 1, further comprising advancing a guidewire towards the treatment site, wherein introducing the delivery sheath comprises introducing the delivery sheath over the guidewire.

7. The method of claim 1, wherein the catheter comprises a balloon catheter.

8. The method of claim 7, further comprising deflating a balloon portion of the balloon catheter following the procedure, and employing the secondary sheath to groom the balloon portion for withdrawal into the delivery sheath after the balloon portion is deflated.

9. The method of claim 8, wherein employing the secondary sheath to groom the balloon portion comprises advancing the secondary sheath over at least a portion of the balloon portion to collapse material of the balloon portion toward an axis of the balloon portion.

10. A system for performing a catheter-based procedure, the system comprising:
    a delivery sheath;
    a secondary sheath that is distinct from the delivery sheath, that has a portion configured to be coaxially advanced through the delivery sheath during a procedure, and that has a default linear shape that is substantially free of radial bias, wherein the secondary sheath has a length that is shorter than a length of the delivery sheath, the secondary sheath further comprising a push member having a distal end attached to a proximal end of the secondary sheath, wherein a combined length of the secondary sheath and the push member exceeds a length of the delivery sheath; and
    a catheter configured to, during the procedure, be advanced through the secondary sheath and delivery sheath and deliver therapy to a treatment site inside a patient's body while the secondary sheath is maintained at a relatively fixed position.

11. The system of claim 10, further comprising a guidewire.

12. The system of claim 11, wherein at least one of the delivery sheath, secondary sheath, or catheter is configured to be advanced toward the treatment site over the guidewire.

13. The system of claim 10, wherein the catheter is a balloon catheter.

14. The system of claim 13, wherein the catheter is configured to delivery cryotherapy to the treatment site.

15. The system of claim 13, wherein the catheter is configured to deliver radio-frequency energy to the treatment site.

16. The system of claim 10, wherein the secondary sheath comprises a distal tip having a tapered outer diameter.

17. The system of claim 16, wherein the distal tip comprises a radio-opaque material.

18. The system of claim 10, wherein the secondary sheath comprises a flexible distal segment and a proximal force-transmitting segment, wherein the flexible distal segment has a greater flexibility than the proximal force-transmitting segment.

19. The system of claim 18, wherein the flexible distal segment comprises a hypotube.

20. The system of claim 18, wherein the proximal force-transmitting segment comprises a braided construction.

21. The system of claim 10, wherein the delivery sheath is steerable.

22. The system of claim 10, wherein the delivery sheath has a lubricious inner surface.

23. The system of claim 22, wherein the inner surface comprises silicone-impregnated HDPE (high-density polyethylene).

24. The system of claim 10, wherein a proximal end of the push member extends proximally out of a proximal end of the delivery sheath such that the proximal end of the push member may be manipulated to advance or retract the secondary sheath.

* * * * *